(12) United States Patent
Miller et al.

(10) Patent No.: US 6,966,648 B2
(45) Date of Patent: Nov. 22, 2005

(54) SYSTEM AND METHOD FOR INCREASING THE DEPTH OF FOCUS OF THE HUMAN EYE

(75) Inventors: David Miller, Brookline, MA (US); Ernesto Blanco, Belmont, MA (US)

(73) Assignee: Boston Innovative Optics, Inc., Irvine, CA (US)

( * ) Notice: Subject to any disclaimer, the term of this patent is extended or adjusted under 35 U.S.C. 154(b) by 0 days.

(21) Appl. No.: 10/729,200

(22) Filed: Dec. 5, 2003

(65) Prior Publication Data

US 2004/0114102 A1   Jun. 17, 2004

Related U.S. Application Data

(62) Division of application No. 10/384,957, filed on Mar. 10, 2003, which is a division of application No. 09/516,258, filed on Feb. 29, 2000, now Pat. No. 6,554,424.

(60) Provisional application No. 60/138,110, filed on Jun. 7, 1999, provisional application No. 60/124,345, filed on Mar. 15, 1999, provisional application No. 60/122,001, filed on Mar. 1, 1999.

(51) Int. Cl.[7] .............................................. G02C 7/10
(52) U.S. Cl. .................. 351/163; 351/160 R; 351/177; 623/6.17
(58) Field of Search .......................... 351/163, 160 R, 351/160 H, 161–162, 165, 177, 44–45, 47; 623/6.11, 6.17

(56) References Cited

U.S. PATENT DOCUMENTS

| 3,270,099 A | 8/1966 | Camp |
| 3,507,566 A | 4/1970 | Knapp |
| 3,578,850 A | 5/1971 | Grant |
| 3,726,587 A | 4/1973 | Kendall |
| 3,794,414 A | 2/1974 | Wesley |
| 4,639,105 A | 1/1987 | Neefe |
| 4,655,774 A | 4/1987 | Choyce |
| 4,955,904 A | 9/1990 | Atebara et al. |
| 4,976,732 A | 12/1990 | Vorosmarthy |
| 4,994,080 A | 2/1991 | Shepard |
| 5,196,026 A | 3/1993 | Barrett et al. |

(Continued)

FOREIGN PATENT DOCUMENTS

| WO | WO 95/08135 | 3/1995 |
| WO | WO 97/48005 | 12/1997 |

OTHER PUBLICATIONS

"Research on the Multi-Range Lens," Wesley, N.K., pp. 18-24.

(Continued)

Primary Examiner—Jordan M. Schwartz
(74) Attorney, Agent, or Firm—Knobbe, Martens, Olson & Bear, LLP

(57) ABSTRACT

A method and apparatus for increasing the depth of focus of the human eye is comprised of a lens body, an optic in the lens body configured to produce light interference, and a pinhole-like optical aperture substantially in the center of the optic. The optic may be configured to produce light scattering or composed of a light reflective material. Alternatively, the optic may increase the depth of focus via a combination of light interference, light scattering, light reflection and/or light absorption. The optic may also be configured as a series of concentric circles, a weave, a pattern of particles, or a pattern of curvatures. One method involves screening a patient for an ophthalmic lens using a pinhole screening device in the lens to increase the patient's depth of focus. Another method comprises surgically implanting a mask in the patient's eye to increase the depth of focus.

34 Claims, 7 Drawing Sheets

U.S. PATENT DOCUMENTS

| | | | |
|---|---|---|---|
| 5,245,367 A | | 9/1993 | Miller et al. |
| 5,260,727 A | | 11/1993 | Oksman et al. |
| 5,314,961 A | | 5/1994 | Anton et al. |
| 5,628,794 A | | 5/1997 | Lindstrom |
| 5,662,706 A | | 9/1997 | Legerton et al. |
| 5,702,440 A | * | 12/1997 | Portney ............... 623/6.28 |
| 5,757,458 A | | 5/1998 | Miller et al. |
| 5,774,202 A | * | 6/1998 | Abraham et al. ........ 351/177 |
| 5,786,883 A | | 7/1998 | Miller et al. |
| 5,864,378 A | | 1/1999 | Portney |
| 5,905,561 A | | 5/1999 | Lee et al. |
| 5,964,748 A | | 10/1999 | Peyman |
| 5,965,330 A | | 10/1999 | Evans et al. |
| 5,980,040 A | | 11/1999 | Xu et al. |
| 6,090,141 A | | 7/2000 | Lindstrom |
| 6,554,424 B1 | | 4/2003 | Miller et al. |

OTHER PUBLICATIONS

"Implants With Coloured and Opaque Portions: Implants With Built-In Stenopeic Aperture," Choyce, P., pp. 21-26; "Uniocular Aphakia Corrected by Anterior Chamber Implants With Built-In Stenoeic Aperture," P. Choyce., pp. 132-136 *Intra-Ocular Lenses and Implants*, London, 1964.

"Use and Interpretation of the Pinhole Test", *The Optometric Weekly*, Takahashi, E., pp. 83-86, 1965.

"New Aspects in the Fitting of the Multi-Range Bifocal Contact Lens", J.J. Groppi, *Contacto*, vol. 15:22-29, 1971.

"The Controlled-Pupil Contact Lens in Low Vision Problems", *Journal of the American Optometic Association*, Rosenbloom, pp. 836-840, 1969.

"Holes in Clear Lenses Demonstrate a Pinhole Effect", *Archives of Opthamology*, Zacharia et al., pp. 511-513, 1988.

"Quantification of the Pinhole Effect", *Perspectives in Refraction*, vol. 21:347-350, Miller et al., 1977.

EPO Partial Search Report, Dated Aug. 18, 2000, PCT/US00/05136.

PCT/US 00/05136 International Preliminary Examination Report, Dated Mar. 15, 2001.

* cited by examiner

SYSTEM AND METHOD FOR INCREASING THE DEPTH OF FOCUS OF THE HUMAN EYE

RELATED APPLICATIONS

This application is a divisional of U.S. patent application Ser. No. 10/384,957, filed Mar. 10, 2003 which is a divisional of U.S. patent application Ser. No. 09/516,258, filed Feb. 29, 2000, now U.S. Pat. No. 6,554,424, which claimed priority from provisional U.S. patent application Ser. No. 60/122,001, filed Mar. 1, 1999, entitled "SCREENING TECHNIQUES AND DEVICES USED PRIOR TO THE INSERTION OF A CORNEAL ANNULUS INLAY;" provisional U.S. patent application Ser. No. 60/124,345, filed Mar. 15, 1999, entitled "NEW METHOD OF INCREASING THE DEPTH OF FOCUS OF THE HUMAN EYE;" and provisional U.S. patent application Ser. No. 60/138,110, filed Jun. 7, 1999, entitled "WOVEN ANNULAR MASK CORNEAL INLAY." The disclosures of all these applications are incorporated herein, in their entirety, by reference.

BACKGROUND OF THE INVENTION

1. Field of the Invention

The invention generally relates to ophthalmic lenses and, more particularly, the invention relates to ophthalmic lenses for increasing the depth of focus of the human eye.

2. Description of the Related Art

It is well-known that the depth of focus of the human eye can be increased with the use of ophthalmic lenses with pinhole-like apertures substantially near the optical center of the lens. For example, U.S. Pat. No. 4,976,732 ("the '732 patent") discloses an ophthalmic lens with a pinhole-like aperture. In the '732 patent, a mask forms the pinhole-like aperture. In one embodiment, the mask is circular in shape. When the pupil is constricted, light enters the retina through the pinhole-like aperture. When the pupil is dilated, light enters the retina through the pinhole-like aperture and the outer edges of the mask.

In addition, U.S. Pat. No. 3,794,414 ("the '414 patent") discloses a contact lens with a pinhole-like aperture. In the '414 patent, the mask forming the pinhole-like aperture has radial slits and/or scalloped edges. In addition, the mask forming the pinhole-like aperture is two spaced-apart concentric circles. However, the radial slits, scalloped edges and two spaced-apart concentric circles promote light diffraction, which in turn reduces the contrast of the image.

In U.S. Pat. Nos. 4,955,904, 5,245,367, 5,757,458 and 5,786,883, various modifications to an ophthalmic lens with a pinhole-like aperture are disclosed. For example, the patents disclose use of an optical power for vision correction in the pinhole-like aperture, or use of an optical power for vision correction in the area outside the mask. In contrast, in U.S. Pat. No. 5,980,040, the mask is powered. In particular, the mask is powered to bend the light passing through the mask to impinge on the retina at a radial distance outside of the fovea. In other words, the mask is powered to "defocus" the light.

In each of these patents, the mask forming the pinhole-like aperture is made, in whole or in part, of a light absorptive material. A light-absorptive material is a material in which light is lost as it passes through the material, generally due to conversion of the light into another form of energy, e.g., heat.

SUMMARY OF THE INVENTION

In accordance with an embodiment of the invention, an ophthalmic lens comprises a lens body, an optic located in the lens body, the optic configured to produce light interference, and a pinhole-like optical aperture substantially in the center of the optic. In a further embodiment of the invention, the optic is configured to positively interfere with parallel light reaching the optic and negatively interfere with diverging light reaching the optic. In addition, some diverging light may pass through the optic. In this alternate embodiment of the invention, the optic is configured to spread out the diverging light passing through the optic.

In an alternate embodiment of the invention, an ophthalmic lens comprises a lens body, an optic located in the lens body, the optic configured to produce light scattering, and a pinhole-like optical aperture substantially in the center of the optic. In a further embodiment of the invention, the optic is configured to forward scatter parallel light reaching the optic and back scatter diverging light reaching the optic.

In another alternative embodiment of the invention, an ophthalmic lens comprises a lens body, an optic located in the lens body, the optic configured to produce light reflection, and a pinhole-like optical aperture substantially in the center of the optic. In an alternate embodiment of the invention, the optic is composed, in whole or in part, of a light reflective material.

In further embodiments of the inventions, the optic may be configured as a series of concentric circles, a weave, a pattern of particles, or a pattern of curvatures. In addition, the pinhole-like aperture includes an optical power for vision correction, and may have a diameter in the range of substantially 0.05 mm to substantially 5.0 mm. Further, the optic may have an outer diameter in the range of substantially 1.0 mm to substantially 8.0 mm. The optic may also be composed of a material having varying degrees of opacity, and the ophthalmic lens and the optic may be composed of a bio-compatible, non-dissolving material, such as polymethyl methacrylate or a medical polymer.

In accordance with another embodiment of the invention, a method for screening a patient for an ophthalmic lens, the ophthalmic lens having a pinhole-like optical aperture, comprises fitting each of the patient's eyes with a first contact lens, placing a mask on each of the first contact lens, the mask configured to produce a pinhole-like aperture in each of the first contact lens, fitting each of the patient's eyes with a second contact lens, the second contact lens being placed over the mask to hold the mask in a substantially constant position, and testing the patient's vision.

In further embodiments of the invention, the mask may be a light interference mask, a light scattering mask, or a light reflective mask. The first contact lens may include an optical power for vision correction. In addition, each of the first and second contact lenses may be soft contact lenses. Further, the mask for each of the patient's eyes may have a light absorption of substantially 100%. In the alternative, the mask for each of the patient's eyes may be composed of a polarized material.

In still further embodiments of the invention, the process of testing comprises testing the patient's acuity for distance vision under bright and dim lighting conditions, testing the patient's acuity for near vision under bright and dim lighting conditions, and testing the patient's contrast sensitivity under bright and dim lighting conditions. The process of testing may further comprise testing a patient's visual acuity using a night driving simulation. The night driving simulation may include a series of objects and road signs under bright and dim lighting conditions, as well as having the patient face a simulated oncoming automobile headlight.

In an alternate embodiment of the invention, the process of testing comprises replacing the mask in one of the patient's eyes with a mask having a light absorption of substantially 85% or less, then, if needed, replacing the mask in the patient's other eye with a mask having a light absorption of substantially 85% or less. Further, the process of testing comprises, if needed, removing the mask from one of the patient's eyes.

In another alternate embodiment of the invention, the process of testing comprises placing an analyzer in the spectacle plane of one of the patient's eyes, the analyzer including a polarizing element, rotating the polarizing element to achieve an optimal balance of contrast and brightness, and determining the resultant light absorption of the mask. In addition, the process of testing may include evaluating the cosmetic appearance of the mask.

In accordance with a still another embodiment of the invention, a method for implanting a mask in a cornea, the mask configured to increase the depth of focus of the human eye, comprises removing the epithelial sheet, creating a depression in the Bowman's membrane, the depression being of sufficient depth and width to expose the top layer of the stroma and accommodate the mask, placing the mask in the depression, and placing the removed epithelial sheet over the mask. In a further embodiment of the invention, the depression may extend into the top layer of the stroma.

In an alternate embodiment of the invention, a method for implanting a mask in a cornea, the mask configured to increase the depth of focus of the human eye, comprises hinging open a portion of the Bowman's membrane, creating a depression in the top layer of the stroma, the depression being of sufficient depth and width to accommodate the mask, placing the mask in the depression, and placing the hinged Bowman's membrane over the mask.

In another alternate embodiment of the invention, a method for implanting a mask in a cornea, the mask configured to increase the depth of focus of the human eye, comprises creating a channel in the top layer of the stroma, the channel being in a plane parallel to the cornea's surface, and placing the mask in the channel. In this embodiment, the mask may be threaded into the channel, or the mask may be injected into the channel.

In still another alternate embodiment of the invention, a method for implanting a mask in a cornea, the mask configured to increase the depth of focus of the human eye, comprises penetrating the top layer of the stroma with an injecting device, and injecting the mask into the top layer of the stroma with the injecting device. In this embodiment, the injecting device may be a ring of needles. In addition, the mask may be a pigment, or the mask may be composed of pieces of pigmented material suspended in a bio-compatible medium. The pigmented material may be made of a medical polymer, e.g., suture material.

In one other alternate embodiment of the invention, a method for implanting a mask in a cornea, the mask configured to increase the depth of focus of the human eye, comprises hinging open a corneal flap, the corneal flap comprising substantially the outermost 20% of the cornea, placing the mask on the cornea, and placing the hinged corneal flap over the mask.

In still one other alternate embodiment of the invention, a method for implanting a mask in a cornea, the mask configured to increase the depth of focus of the human eye, comprises creating a pocket in the stroma, the pocket being of sufficient size to accommodate the mask, and placing the mask in the created pocket.

In further embodiments of the inventions, the mask may be a light interference optic, a light scattering optic, or a light reflective optic. In addition, the mask may block visual aberrations. In addition, after surgery, a contact lens may be placed over at least the affected portion of the cornea.

BRIEF DESCRIPTION OF THE DRAWINGS

The foregoing and other objects and advantages of the invention will be appreciated more fully from the following further description thereof with reference to the accompanying drawings wherein.

DETAILED DESCRIPTION OF THE PREFERRED EMBODIMENT

In accordance with an embodiment of the invention, an ophthalmic lens (e.g., a contact lens, an intra ocular lens, a corneal inlay lens, etc.) increases the depth of focus of the human eye through the use of an optic. The optic surrounds a pinhole-like optical aperture near the optical center of the lens. The pinhole-like aperture in conjunction with the optic increases the depth of focus of the human eye. In particular, the optic increases the depth of focus of the human eye using light interference, light scattering, light reflection, light absorption and/or a combination of one or more of these properties. An optic configured in accordance with the various embodiments of the invention is referred to as a Paraxial Adaptive Optic™.

Figure 1A:
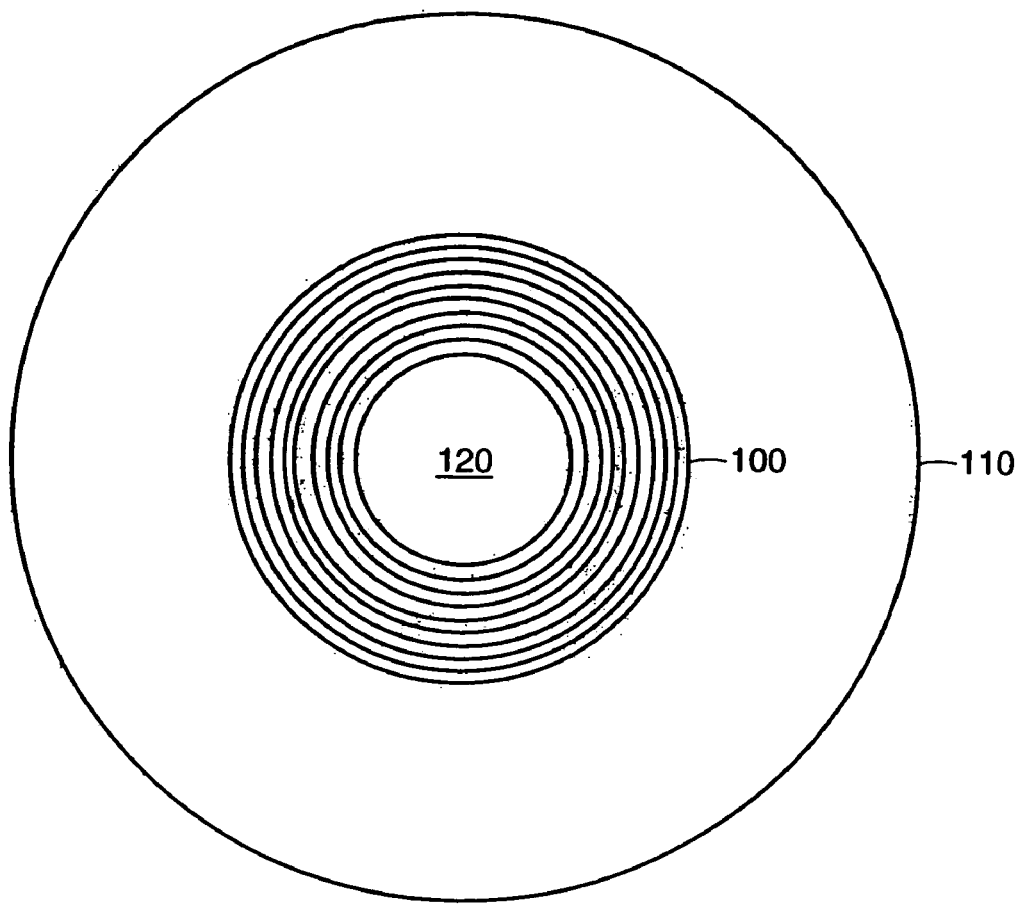
FIGS. 1a and 1b show an exemplary ophthalmic lens with an exemplary optic configured to produce light interference.
Figure 1B:
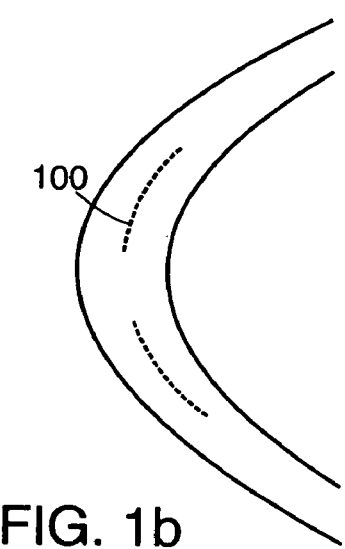

FIGS. 1a and 1b show an exemplary ophthalmic lens with an exemplary optic configured to produce light interference. FIG. 1a shows a front view of the exemplary ophthalmic lens. FIG. 1b shows a side view of the exemplary optic implanted in the cornea of a human eye.

Light interference is the additive process in which the amplitude of two or more overlapping light waves is either attenuated or reinforced. For example, when two overlapping light waves are in-phase (the crest and trough of one wave coincides with the crest and trough of the other wave), then the amplitude of the resultant light wave is reinforced. This type of interference is referred to as positive interference. In contrast, when two overlapping light waves are out-of-phase (the crest of one wave coincides with the trough of the other wave), then the amplitude of the resultant light wave is attenuated. This type of interference is referred to as negative interference. Of course, light interference also occurs between the two extremes of in-phase and out-of-phase.

As shown in FIGS. 1a and 1b, optic 100 is located substantially in the center of lens body 110. Optic 100 surrounds optical aperture 120 located near the optical center of lens body 110. The specific location of optical aperture 120 in lens body 110 varies in accordance with the patient's eye. Specifically, optical aperture 120 is positioned in lens body 10 to be concentric with the patient's pupil.

In operation, optical aperture 120 increases the depth of focus of the human eye via a "pinhole effect." In particular, optical aperture 120 increases depth of focus by limiting the light reaching the retina to plane wavefront light. In photonics, a wavefront is a surface connecting all points equidistant from a source. Plane wavefront light is relatively parallel light, e.g., light from a distant source. It is "relatively" parallel light because, in reality, even light from a distant star is diverging light. In contrast, convex wavefront light is relatively diverging light, e.g., light from a near source. It is easier for the human eye to focus plane wavefront light because the crystalline lens of the human eye can focus parallel light on the retina with little or no accommodation. In accommodation, the crystalline lens, through the action of the ciliary muscles, thickens and, thereby, changes its degree of curvature.

In order to achieve a useful "pinhole effect," optical aperture 120 should have a diameter in the range of substantially 0.05 millimeters ("mm") to substantially 5.0 mm. In addition, in order to aid examination of the retina and increase brightness when the pupil is dilated, the outer diameter of optic 100 should be in the range of substantially 1.0 mm to substantially 8.0 mm. Moreover, to further improve vision, optical aperture 120 may include an optical power for vision correction, e.g., correction for near vision, correction for distance vision, correction for intermediate vision, etc. Also, the area outside optic 100 may include an optical power for vision correction.

In operation, optic 100 increases the depth of focus of the human eye via its configuration. In particular, optic 100 is configured to produce light interference via a series of concentric circles. Specifically, optic 100 is configured to reinforce relatively parallel light and attenuate relatively diverging light. When optic 100 attenuates less than all of the relatively diverging light, then optic 100 is further configured to spread out the diverging light that passes through optic 100, i.e., weakening the diverging light passing through optic 100. Thus, because diverging light is attenuated and/or weakened, the "pinhole effect" of optical aperture 120 is increased for relatively near objects, producing a higher contrast depth of focus image of relatively near objects. Moreover, because parallel light is reinforced, the "pinhole effect" of optical aperture 120 is reduced, producing a brighter image of relatively distant objects.

Optic 100 is also configured to effect the chromatic aberration of the human eye. The human eye's chromatic aberration, in which the size of an image appears to change when the color of the image is changed, results from the normal increase in refractive index toward the blue end of the color spectrum. In optic 100, the increase in refractive index is toward the red end of the color spectrum. Thus, optic 100 may reduce or cancel the chromatic aberration of the human eye.

Further, optic 100 is configured to meet the specific needs of the patient. For example, a person of skill in the art understands that, among other things, the addition of concentric circles, the removal of concentric circles, the change in spacing between concentric circles, the varying of spacing between concentric circles, and the shape of the concentric circles (e.g., oval, round, elliptical, etc.) would influence the light interference properties of optic 100.

Figure 2A:
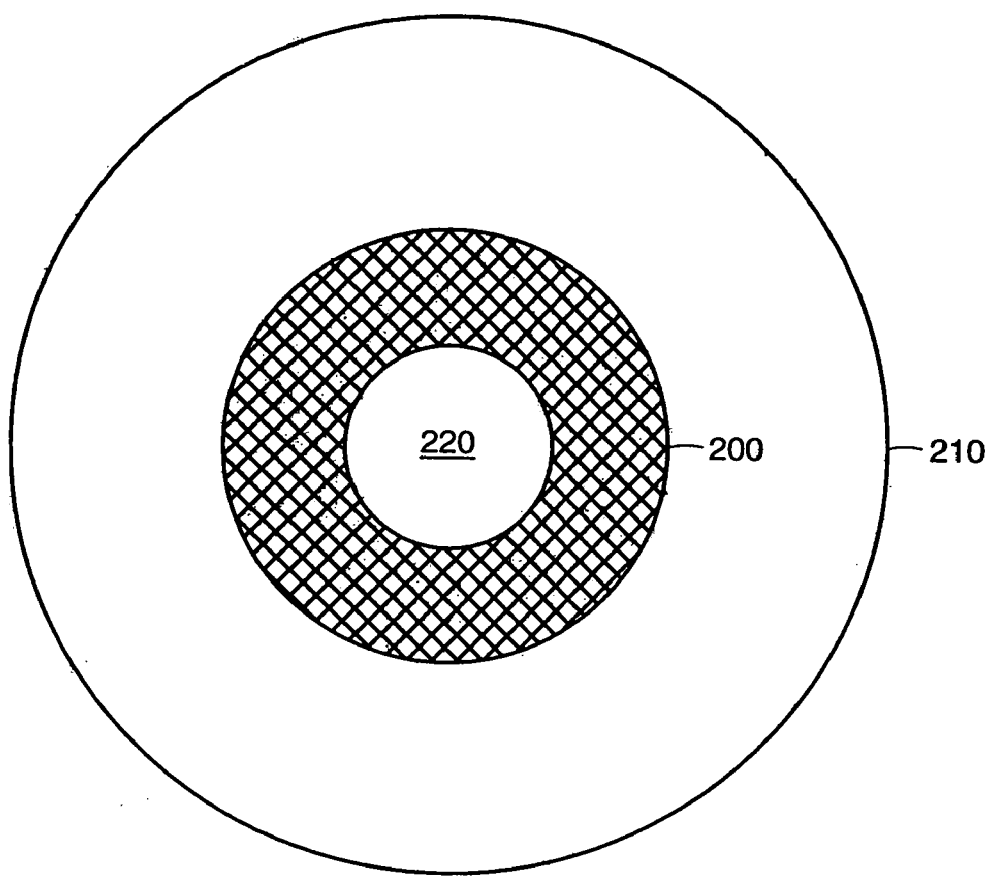
FIGS. 2a and 2b show another exemplary ophthalmic lens with another exemplary optic configured to produce light interference.
Figure 2B:
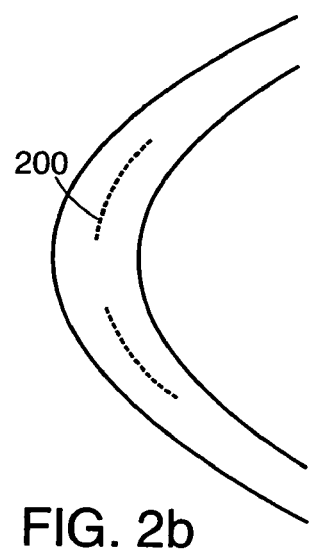

FIGS. 2a and 2b show another exemplary ophthalmic lens with another exemplary optic configured to produce light interference. In this exemplary embodiment, optic 200 is configured to produce light interference via a weave. As discussed in regard to optic 100, the weave reinforces relatively parallel light and attenuates relatively diverging light. Depending on the weave's material, the weave may also absorb light coming into contact with the weave's material. FIG. 2a shows a front view of the exemplary ophthalmic lens. FIG. 2b shows a side view of the exemplary optic implanted in the cornea of a human eye.

As discussed in regard to optic 100, optic 200 is configured to meet the specific needs of the patient. For example, a person of skill in the art understands that, among other things, the density of the weave would influence the light interference properties of optic 200.

Figure 3A:
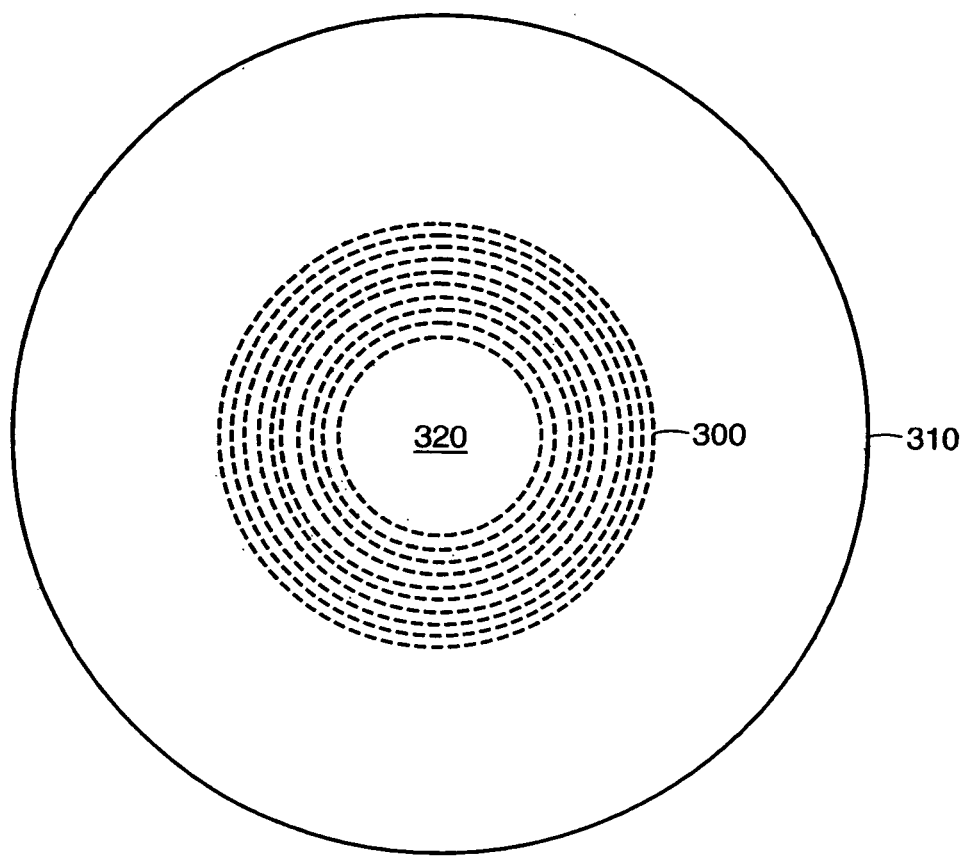
FIGS. 3a and 3b show an exemplary ophthalmic lens with an exemplary optic configured to produce light scattering.
Figure 3B:
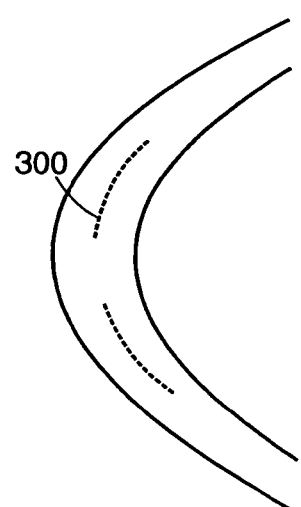

FIGS. 3a and 3b show an exemplary ophthalmic lens with an exemplary optic configured to produce light scattering. FIG. 3a shows a front view of the exemplary ophthalmic lens. FIG. 3b shows a side view of the exemplary optic implanted in the cornea of a human eye.

In general, light scattering is the deflection of light upon interaction with a medium. Light is forward scattered when, upon interaction with a medium, it is deflected through angles of 90°. or less with respect to the original direction of motion. Light is back scattered when, upon interaction with a medium, it is deflected through angles in excess of 90°. with respect to the original direction of motion.

As shown in FIGS. 3a and 3b, optic 300 is located substantially in the center of lens body 310. Optic 300 surrounds optical aperture 320 located near the optical center of lens body 310. The specific location of optical aperture 320 in lens body 310 varies in accordance with the patient's eye. Specifically, optical aperture 320 is positioned in lens body 310 to be concentric with the patient's pupil.

As discussed in regard to optical apertures 120 and 220, optical aperture 320 increases the depth of focus of the human eye via a "pinhole effect." Similarly, as discussed in regard to optics 100 and 200, optic 300 increases the depth of focus of the human eye via its configuration. In particular, optic 300 is configured to produce light scattering via a pattern of particles. Specifically, optic 300 is configured to forward scatter relatively parallel light and back scatter relatively diverging light. Thus, because diverging light is back scattered, the "pinhole effect" of optical aperture 320 is increased for relatively near objects, producing a higher contrast depth of focus image of relatively near objects. Moreover, because parallel light is forward scattered, the "pinhole effect" of optical aperture 320 is reduced, producing a brighter image of relatively distant objects.

Further, optic 300 is configured to meet the specific needs of the patient. For example, a person of skill in the art understands that, among other things, the light absorption of the particles, the index of refraction of the particles, the index of refraction of the media surrounding the particles, the size of the particles, and the space between the particles would influence the light scattering properties of optic 300. In addition, optic 300 may be configured to produce light interference, as discussed in regard to optics 100 and 200.

Figure 4A:
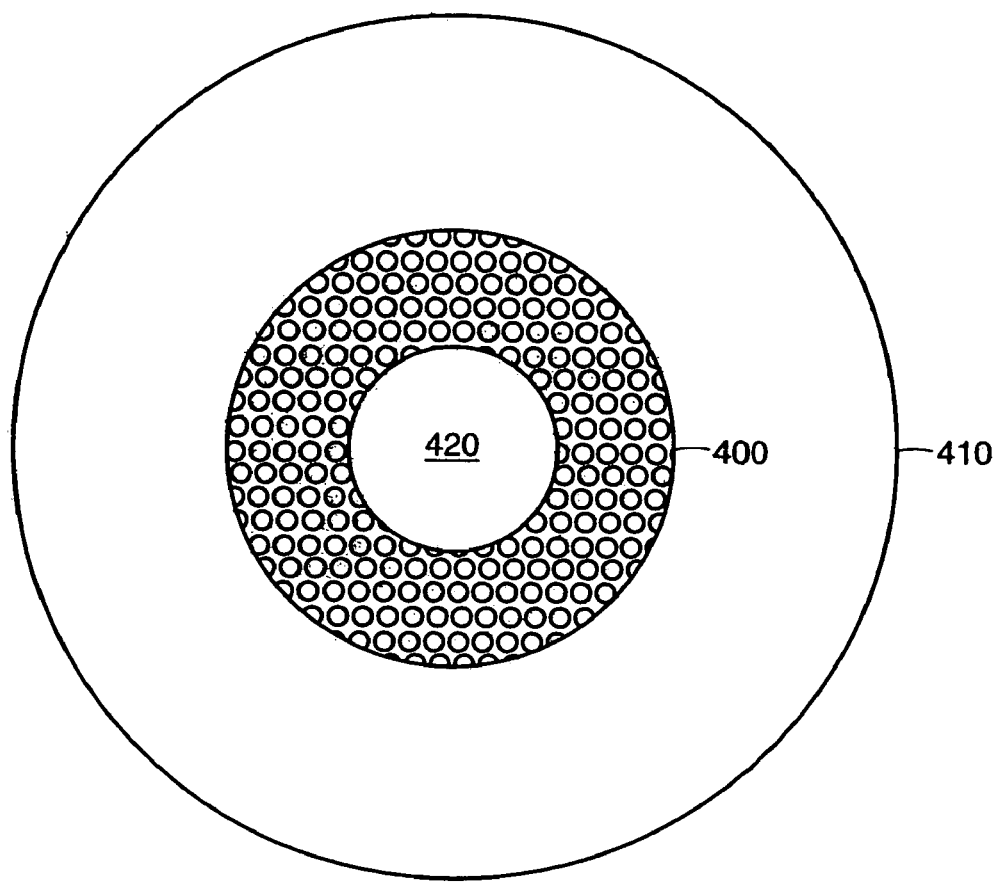
FIGS. 4a and 4b show an exemplary ophthalmic lens with an exemplary optic configured to produce light reflection.
Figure 4B:
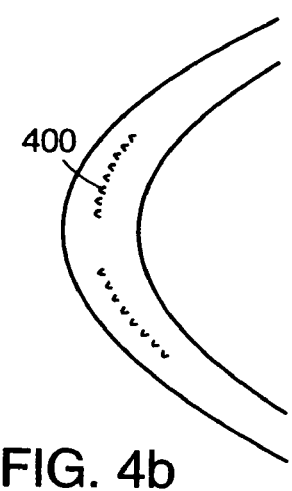

FIGS. 4a and 4b show an exemplary ophthalmic lens with an exemplary optic configured to produce light reflection. FIG. 4a shows a front view of the exemplary ophthalmic lens. FIG. 4b shows a side view of the exemplary optic implanted in the cornea of a human eye.

Optic 400 is located substantially in the center of lens body 410. Optic 400 surrounds optical aperture 420 located near the optical center of lens body 410. The specific location of optical aperture 420 in lens body 410 varies in accordance with the patient's eye. Specifically, optical aperture 420 is positioned in lens body 410 to be concentric with the patient's pupil.

As discussed in regard to optical apertures 120, 220 and 320, optical aperture 420 increases the depth of focus of the human eye via a "pinhole effect." Similarly, as discussed in regard to optics 100, 200 and 300, optic 400 increases the depth of focus of the human eye via its configuration. In particular, optic 400 is configured to reflect light, in whole or in part, via a pattern of curvatures. Specifically, optic 400 is configured to favor transmission of the light to which the retinal rods are more sensitive, i.e., dim light and/or blue light, and to block the light to which retinal cones are more sensitive, i.e., bright light. Thus, because bright light is blocked, the "pinhole effect" of optical aperture 420 is increased for relatively near objects, producing a higher contrast depth of focus image of relatively near objects. Moreover, because dim light and/or blue light is transmitted, the "pinhole effect" of optical aperture 420 is reduced, producing a brighter image of relatively distant objects.

In an alternate embodiment, optic 400 may be composed, in whole or in part, of a light reflective material. A light reflective material is a material that, in whole or in part, reflects back light coming into contact with the material.

Further, optic 400 may be configured to meet the specific needs of the patient. For example, a person of skill in the art understands that, among other things, the type of material, the thickness of material, and the curvature of material would influence the light reflective properties of optic 400. In addition, optic 400 may be configured to produce light interference and/or light scattering, as discussed in regard to optics 100, 200 and 300, respectively.

In a particular embodiment of the ophthalmic lens described in FIG. 4, optic 400 is composed of a light reflective material with a peak transmission of substantially 550 nanometers ("nm"). A light-adapted retina has a peak transmission at 550 nm. In contrast, a dark-adapted retina has a peak transmission at 500 nm. Thus, an optic with a peak transmission of substantially 550 nm filters out more light with a peak transmission of 500 nm, i.e., bright light, than light with a peak transmission of 550 nm, i.e., dim light. Thus, as discussed above, because bright light is blocked, the "pinhole effect" of optical aperture 420 is increased for relatively near objects, producing a higher contrast depth of focus image of relatively near objects. Moreover, because dim light is transmitted, the "pinhole effect" of optical aperture 420 is reduced, producing a brighter image of relatively distant objects.

Further, this particular embodiment of optic 400 may be configured to meet the specific needs of the patient. For example, a person of skill in the art understands that, among other things, the peak transmission of the mask may be changed, e.g., to a peak transmission of 500 nm. In addition, the mask may be composed of material, other than light reflective material, which also allows the desired peak transmissions.

In alternate embodiments, the optic is composed of biocompatible, non-dissolving material, e.g., polymethyl methacrylate or medical polymers. In addition, the optic may be composed, in whole or in part, of a light reflective material or, in whole or in part, of a light absorptive material. Further, the optic may be composed, in whole or in part, of a material having varying degrees of opacity. The optic may also be configured to produce light interference, light-scattering and light reflection, or some combination of one or more of these properties. Moreover, the optic may be colored to match the color of a patient's iris.

In accordance with a further embodiment of the invention, a patient interested in an ophthalmic lens with a pinhole-like aperture is screened using soft contact lenses and a mask, referred to as a pinhole screening device. The mask may be an optic as described in the prior art, an optic as described herein, or an optic combining one or more of these properties. After insertion of the pinhole screening device, the patient's vision is tested.

Figure 5:
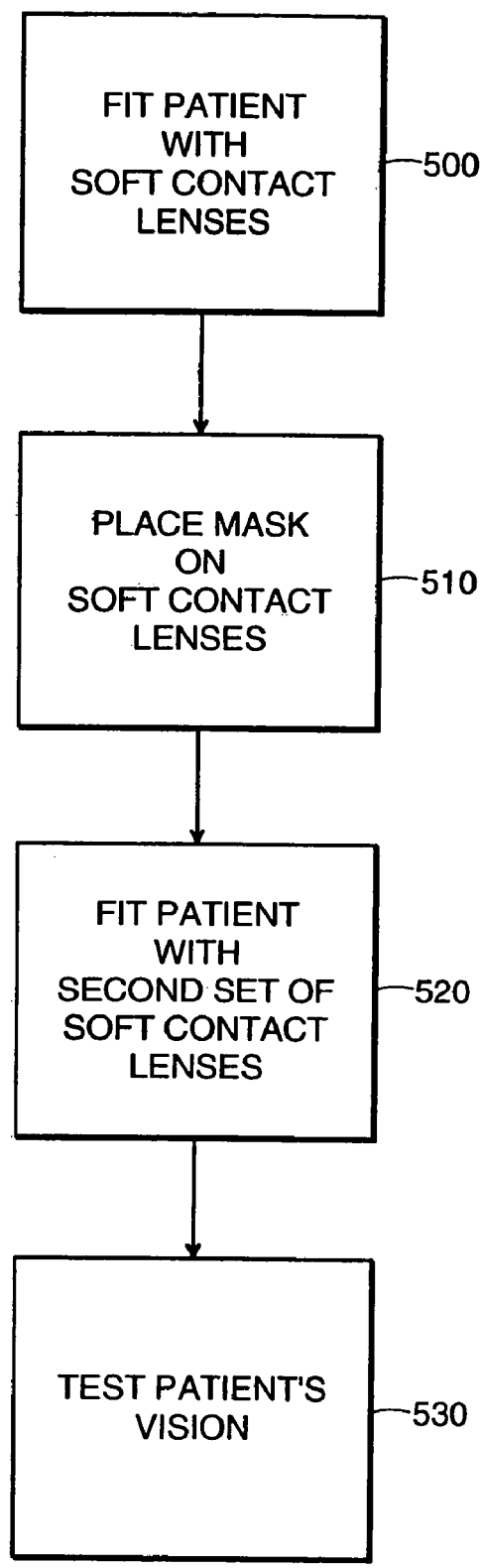
FIG. 5 shows an exemplary process for screening a patient interested in an ophthalmic lens with a pinhole-like aperture using an exemplary pinhole screening device.

FIG. 5 shows an exemplary process for screening a patient interested in an ophthalmic lens with a pinhole-like aperture using an exemplary pinhole screening device. The process begins at step 500, in which the patient is fitted with soft contact lenses, i.e., a soft contact lens in placed in each of the patient's eyes. If needed, the soft contact lenses may include vision correction. Next, at step 510, a mask is placed on the soft contact lenses. The mask should be placed concentric with the patient's pupil. In addition, the curvature of the mask should parallel the curvature of the patient's cornea. The process continues at step 520, in which the patient is fitted with a second set of soft contact lenses, i.e., a second soft contact lens is placed over the mask in each of the patient's eyes. The second contact lens holds the mask in a substantially constant position. Last, at step 530, the patient's vision is tested. During testing, it is advisable to check the positioning of the mask to ensure it remains concentric with the patient's pupil.

A test of the patient's vision may include testing the patient's acuity for distance vision under bright and dim lighting conditions, testing the patient's acuity for near vision under bright and dim lighting conditions, and testing the patient's contrast sensitivity under bright and dim lighting conditions. In addition, the test may include testing the patient's visual acuity using a night driving simulation. A night driving simulation may include a series of objects and road signs under bright and dim lighting conditions, as well as a simulated oncoming automobile headlight.

The test of the patient's vision may further include changing the mask. For example, the test might first be conducted using, in each of the patient's eyes, a mask having a light absorption of substantially 100%. If, for example, the patient experiences a sense of dimness, the mask in one of the patient's eyes may be replaced with a mask having a light absorption of substantially 85%. If, for example, the sense of dimness continues, the mask in the patient's other eye may be replaced with a mask having a light absorption of substantially 85%. Then, for example, if the sense of dimness continues, the mask may be removed from one of the patient's eyes.

In the alternate, the mask in one of the patient's eyes may be replaced with a mask having a light absorption less than substantially 85%. If, for example, the patient experiences a sense of dimness with a mask having a light absorption of substantially 100%, then the mask in one of the patient's eyes may be replaced with a mask having a light absorption of substantially 75%. If, for example, the sense of dimness continues, the mask in the patient's other eye may be replaced with a mask having a light absorption of substantially 75%. Then, for example, if the sense of dimness continues, the 75% mask may be replaced with a mask having a light absorption of substantially 50%.

As can be seen, there are numerous permutations for thoroughly screening the patient to find the optimal balance of contrast and brightness. In effect, the, mask in each of the patient's eyes is replaced, every other time, with a mask having a different light absorption than the replaced mask. This process continues until the optimal balance of contrast and brightness is found.

The process for changing the mask while testing the patient's vision also includes changing from an optic as described in the prior art to an optic as described herein. In addition, various mask configurations may be used. For example, an optic having both light interference and light scattering may be used, or an optic having both light reflective and light absorptive properties may be used. Once again, the numerous permutations allow for thoroughly screening the patient to find the optimal balance of contrast and brightness prior to, for example, the doctor placing a customized order or the patient undergoing invasive surgery.

The test of the patient's vision may also include evaluating the cosmetic appearance of the mask. For example, if the patient is dissatisfied with the appearance of the mask, the mask can be replaced with a mask of appropriate configuration colored to match the patient's iris.

In an alternate testing process, the mask placed on the soft contact lens in each of the patient's eyes is composed of a polarized material. A polarized material has a light absorption of substantially 50%. Then, an analyzer, which contains a polarized element, is used to help calculate the patient's optimal light absorption properties for the mask. In the process, the analyzer is placed in the spectacle plane of one of the patient's eyes and the polarized element in the analyzer is rotated until the patient experiences an optimal balance of contrast and brightness. The process may be repeated for the patient's other eye.

Using the analyzer, the doctor may now calculate the resultant light absorption of the mask. If desired, a mask of similar light absorption, whether it be an optic as described in the prior art, an optic as described herein, or an optic combining one or more of these properties, can now be placed between the contact lenses in each of the patient's eyes and the patient's vision tested, as described above.

In accordance with a still further embodiment of the invention, a mask is surgically implanted into the eye of a patient interested in increasing his or her depth of focus. For example, the patient may suffer from presbyopia, a condition in which the crystalline lens can no longer accommodate near vision because of a loss of elasticity in the lens or a weakness in the ciliary muscle. The mask may be an optic as described in the prior art, an optic as described herein, or an optic combining one or more of these properties. Further, the mask may be configured to correct visual aberrations. To aid the surgeon surgically implanting a mask into a patient's eye, the mask may be pre-rolled or folded for ease of implantation.

The mask may be implanted in several locations. For example, the mask may be implanted underneath the cornea's epithelium sheet, beneath the cornea's Bowman membrane, in the top layer of the cornea's stroma, or in the cornea's stroma. When the mask is placed underneath the cornea's epithelium sheet, removal of the mask requires little more than removal of the cornea's epithelium sheet.

Figure 6A:
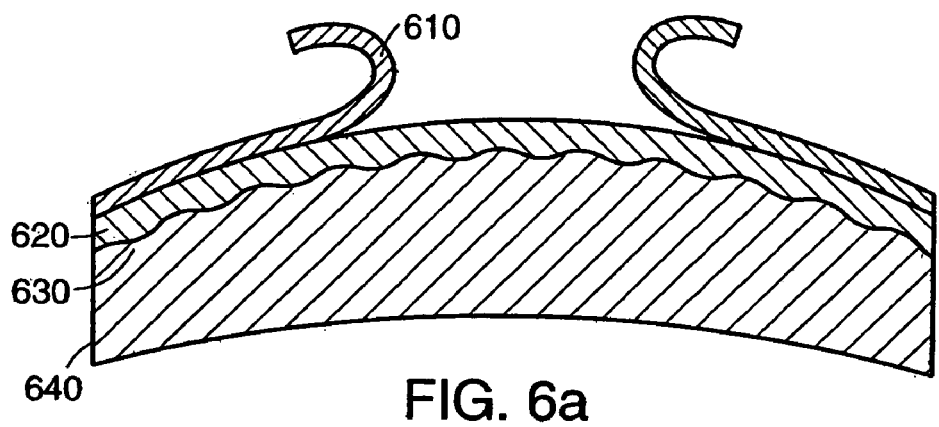
FIGS. 6a through 6c show a mask, configured to increase the depth of focus of the human eye, inserted underneath the cornea's epithelium sheet.
Figure 6B:
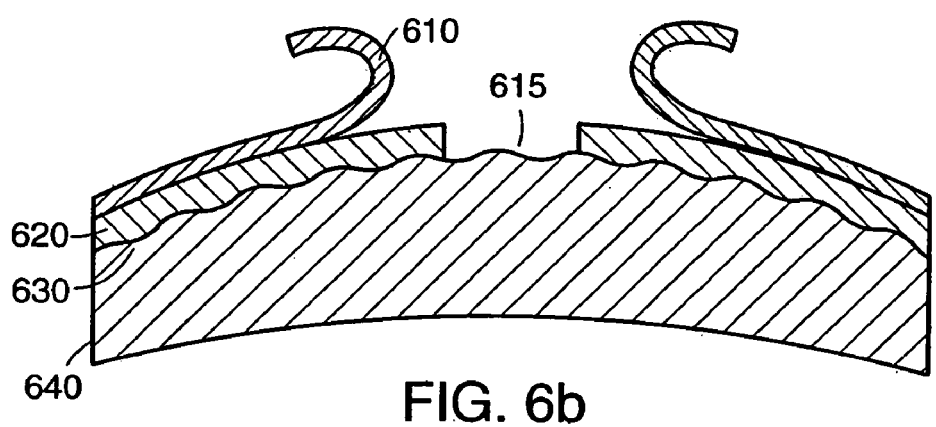
Figure 6C:
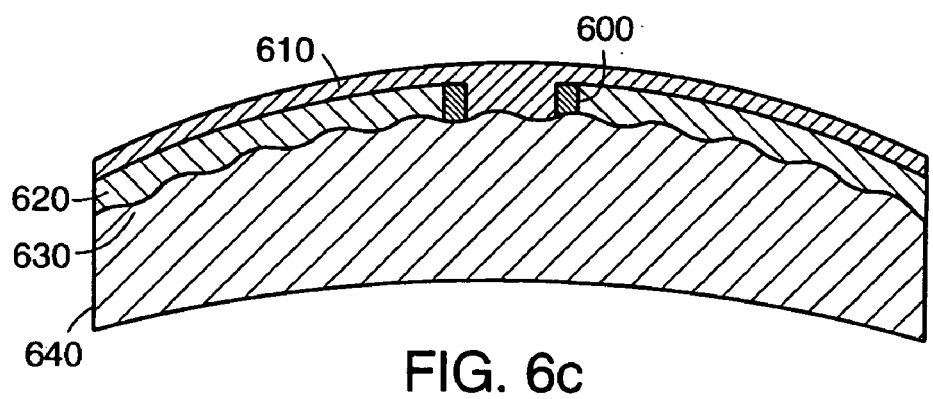

FIGS. 6a through 6c show mask 600 inserted underneath epithelium sheet 610. In this embodiment, the surgeon first removes epithelium sheet 610. For example, as shown in FIG. 6a, epithelium sheet 610 may be rolled back. Then, as shown in FIG. 6b, the surgeon creates depression 615 in Bowman's member 620. Depression 615 should be of sufficient depth and width to both expose top layer 630 of stroma 640 and to accommodate mask 600. Mask 600 is then placed in depression 615. Last, epithelium sheet 610 is placed over mask 600. Over time, as shown in FIG. 6c, epithelium sheet 610 will grow and adhere to top layer 630 of stroma 640, as well as mask 600 depending, of course, on the composition of mask 600. As needed, a contact lens may be placed over the incised cornea to protect the mask.

Figure 7A:
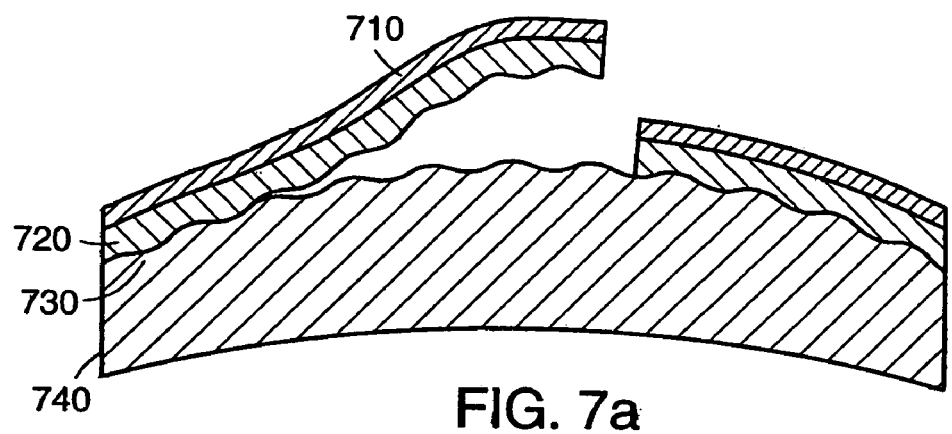
FIGS. 7a through 7c show a mask, configured to increase the depth of focus of the human eye, inserted beneath the cornea's Bowman's membrane.
Figure 7B:
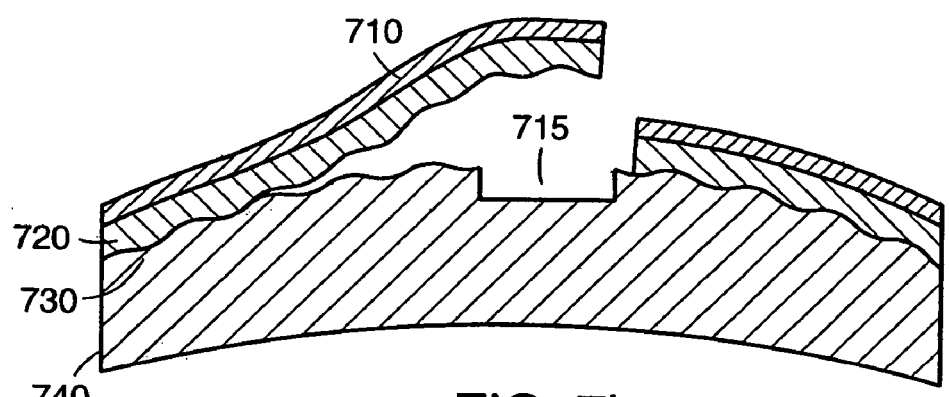
Figure 7C:
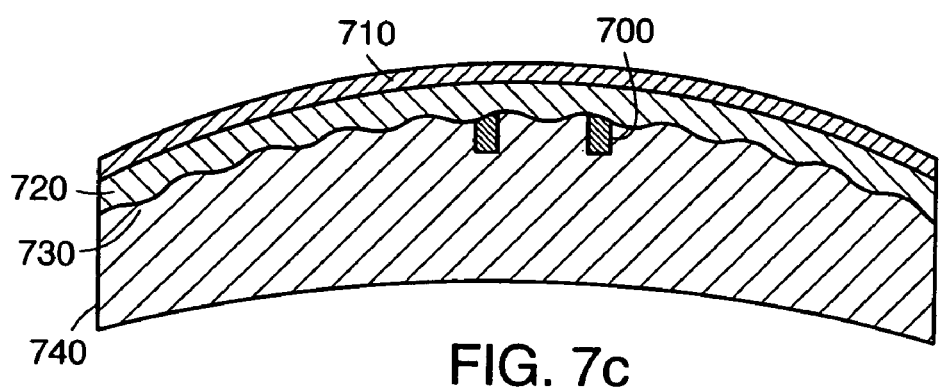

FIGS. 7a through 7c show mask 700 inserted beneath Bowman's membrane 720. In this embodiment, as shown in FIG. 7a, the surgeon first hinges open Bowman's member 720. Then, as shown in FIG. 7b, the surgeon creates depression 715 in top layer 730 of stroma 740. Depression 715 should be of sufficient depth and width to accommodate mask 700. Then, mask 700 is placed in depression 715. Last, Bowman's member 720 is placed over mask 700. Over time, as shown in FIG. 7c, epithelium sheet 710 will grow over the incised area of Bowman's member 720. As needed, a contact lens may be placed over the incised cornea to protect the mask.

In an alternate embodiment, a mask of sufficient thinness, i.e., less than substantially 20 microns, may be placed underneath epithelium sheet 610, or beneath Bowman's member 720, without creating a depression in the top layer of the stroma.

In an alternate method for surgically implanting a mask in the eye of a patient, the mask may be threaded into a channel created in the top layer of the stroma. In this method, a curved channeling tool creates a channel in the top layer of the stroma, the channel being in a plane parallel to the surface of the cornea. The channeling tool either pierces the surface of the cornea or, in the alternative, is inserted via a small superficial radial incision. In the alternative, a laser focusing an ablative beam may create the channel in the top layer of the stroma. In this embodiment, the mask may be a single segment with a break, or it may be two or more segments.

In another alternate method for surgically implanting a mask in the eye of a patient, the mask may be injected into the top layer of the stroma. In this embodiment, an injection tool with a stop penetrates the surface of the cornea to the specified depth. For example, the injection tool may be a ring of needles capable of producing a mask with a single injection. In the alternative, a channel may first be created in the top layer of the stroma. Then, the injector tool may inject the mask into the tunnel. In this embodiment, the mask may be a pigment, or it may be pieces of pigmented material suspended in a bio-compatible medium. The pigment material may be made of a polymer or, in the alternative, made of a suture material.

In still another alternate method for surgically implanting a mask in the eye of the mask may be placed beneath the corneal flap created during keratectomy, when the outermost 20% of the cornea is hinged open.

In one still other alternate method for surgically implanting a mask in the eye of the mask may be placed in a pocket created in the cornea's stroma.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. An ophthalmic device for insertion into a cornea of an eye, the eye having a retina including retinal rods and retinal cones, the device comprising:
   an optic comprising a first zone and a second zone, the first zone being substantially completely transmissive, the second zone being configured to filter light to favor transmission of light to which the retinal rods are generally more sensitive;
   whereby depth of focus is increased and contrast is increased for relatively near objects
   wherein the second zone filters light by reflecting a portion of the light reaching the second zone; and
   wherein the second zone has a transmissive peak at about 550 nm.

2. The ophthalmic device of claim 1, further comprising an aperture substantially in the center of the optic.

3. The ophthalmic device of claim 1, wherein the optic comprises a light reflective material.

4. The ophthalmic device of claim 1, wherein the optic comprises a pattern of curvatures.

5. The ophthalmic device of claim 1, wherein the optic is configured as a series of concentric circles.

6. The ophthalmic device of claim 1, wherein the optic is configured as a set of particles.

7. The ophthalmic device of claim 1, wherein the optic comprises an aperture that includes an optical power for vision correction.

8. The ophthalmic device of claim 1, wherein the optic comprises an aperture that has a diameter in the range of about 0.05 mm to about 5.0 mm.

9. The ophthalmic device of claim 1, wherein the optic has an outer diameter in the range of about 1.0 mm to about 8.0 mm.

10. The ophthalmic device of claim 1, wherein the optic is configured to block light to which retinal cones are generally more sensitive.

11. The ophthalmic device of claim 10, wherein the optic is configured to favor transmission of dim light or blue light.

12. The ophthalmic device of claim 10, wherein the optic is configured to block transmission of bright light.

13. The ophthalmic device of claim 12, wherein the optic is configured to favor transmission of dim light or blue light.

14. The ophthalmic device of claim 1, wherein the optic is configured to favor transmission of dim light or blue light.

15. An ophthalmic device for insertion into a cornea of an eye, the eye having a retina including retinal rods and retinal cones, the device comprising:
   an optic comprising a first zone and a second zone, the first zone being substantially completely transmissive, the second zone being configured to filter light to favor transmission of light to which the retinal rods are generally more sensitive;
   whereby depth of focus is increased and contrast is increased for relatively near objects; and
   wherein the second zone filters light by reflecting a portion of the light reaching the second zone; and
   wherein the second zone has a transmissive peak at about 500 nm.

16. The ophthalmic device of claim 15, further comprising an aperture substantially in the center of the optic.

17. The ophthalmic device of claim 15, wherein the optic comprises a light reflective material.

18. The ophthalmic device of claim 15, wherein the optic comprises a pattern of curvatures.

19. The ophthalmic device of claim 15, wherein the optic is configured as a series of concentric circles.

20. The ophthalmic device of claim 15, wherein the optic is configured as a weave.

21. The ophthalmic device of claim 15, wherein the optic is configured as a set of particles.

22. The ophthalmic device of claim 15, wherein the optic comprises an aperture that includes an optical power for vision correction.

23. The ophthalmic device of claim 15, wherein the optic comprises an aperture that has a diameter in the range of about 0.05 mm to about 5.0 mm.

24. The ophthalmic device of claim 15, wherein the optic has an outer diameter in the range of about 1.0 mm to about 8.0 mm.

25. The ophthalmic device of claim 15, wherein the optic is configured to block light to which retinal cones are generally more sensitive.

26. The ophthalmic device of claim 25, wherein the optic is configured to favor transmission of dim light or blue light.

27. The ophthalmic device of claim 25, wherein the optic is configured to block transmission of bright light.

28. The ophthalmic device of claim 27, wherein the optic is configured to favor transmission of dim light or blue light.

29. The ophthalmic device of claim 15, wherein the optic is configured to favor transmission of dim light or blue light.

30. An ophthalmic device for insertion into a cornea of an eye, the eye having a retina including retinal rods and retinal cones, the device comprising:
   an optic comprising a first zone and a second zone, the first zone being substantially completely transmissive, the second zone being configured to filter light to favor transmission of light to which the retinal rods are generally more sensitive;
   whereby depth of focus is increased and contrast is increased for relatively near objects; and
   wherein the optic is configured as a weave.

31. A method for increasing the depth of focus of the human eye, the method comprising:
   providing an optic comprising a first zone and a second zone, the first zone being substantially completely transmissive, the second zone being configured to filter light to favor transmission of light to which the retinal rods are generally more sensitive; and
   inserting the ophthalmic device into the cornea; and
   wherein the optic comprises a weave.

32. The method of claim 31, wherein the optic comprises an aperture that includes an optical power for vision correction.

33. The method of claim 31, wherein the optic comprises an aperture that has a diameter in the range of about 0.05 mm to about 5.0 mm.

34. The method of claim 31, wherein the optic has an outer diameter in the range of about 1.0 mm to about 8.0 mm.

* * * * *